US010568608B2

(12) United States Patent
Martins

(10) Patent No.: US 10,568,608 B2
(45) Date of Patent: Feb. 25, 2020

(54) ULTRASOUND COLOR FLOW IMAGING

(71) Applicant: B-K MEDICAL APS, Herlev (DK)

(72) Inventor: Bo Martins, Rodovre (DK)

(73) Assignee: B-K Medical Aps, Herlev (DK)

( * ) Notice: Subject to any disclaimer, the term of this patent is extended or adjusted under 35 U.S.C. 154(b) by 812 days.

(21) Appl. No.: 15/177,659

(22) Filed: Jun. 9, 2016

(65) Prior Publication Data

US 2017/0354398 A1  Dec. 14, 2017

(51) Int. Cl.
*A61B 8/08* (2006.01)
*G01S 7/52* (2006.01)
*A61B 8/00* (2006.01)

(52) U.S. Cl.
CPC .......... *A61B 8/5207* (2013.01); *A61B 8/4483* (2013.01); *A61B 8/463* (2013.01); *A61B 8/467* (2013.01); *A61B 8/5246* (2013.01); *G01S 7/52085* (2013.01)

(58) Field of Classification Search
CPC ..... A61B 8/5207; A61B 8/5246; A61B 8/463; A61B 8/5269; A61B 8/5276; G01S 7/52085; G06K 9/00234; G06T 7/00; G06T 7/136
See application file for complete search history.

(56) References Cited

U.S. PATENT DOCUMENTS

| | | | | |
|---|---|---|---|---|
| 5,623,929 A * | 4/1997 | Weng | .................. | G01S 7/52071 600/455 |
| 6,526,163 B1 * | 2/2003 | Halmann | ............ | G01S 7/52044 382/128 |
| 6,563,874 B1 * | 5/2003 | Lu | .......................... | H04N 19/51 348/699 |
| 2011/0218435 A1 * | 9/2011 | Srinivasan | ............... | A61B 8/06 600/441 |
| 2013/0044952 A1 * | 2/2013 | Du | .......................... | G06K 9/38 382/170 |
| 2015/0297189 A1 * | 10/2015 | Shishido | ............. | G01S 7/52034 600/443 |

OTHER PUBLICATIONS

Grahn, Alexander. "An Image and Processing Comparison Study of Antialiasing Methods." (2016), Blekinge Institute of Technology, pp. 1-44 (Year: 2016).*

* cited by examiner

*Primary Examiner* — Bo Joseph Peng
(74) *Attorney, Agent, or Firm* — Anthony M. Del Zoppo, III; Daugherty & Del Zoppo Co. LPA

(57) ABSTRACT

A method includes receiving ultrasound echo signals produced in response to a pulsed ultrasound field interacting with anatomical tissue and flow of structure therein. The method further includes generating electrical signals indicative thereof. The method further includes beamforming the electrical signals producing beamformed data. The method further includes constructing a real-time image of the anatomical tissue with the beamformed data. The method further includes constructing a de-aliased color images of the flow with the beamformed data. The method further includes visually presenting the real-time image of the anatomical tissue with the de-aliased color images of the flow superimposed thereover.

14 Claims, 4 Drawing Sheets

ULTRASOUND COLOR FLOW IMAGING

TECHNICAL FIELD

The following generally relates to ultrasound imaging and more particularly to color flow imaging.

BACKGROUND

Ultrasound imaging provides a real-time image (e.g., a B-mode image) with structural information about the interior of a subject such as organs and blood vessels. Ultrasound imaging has additionally been used to concurrently visualize flow inside the blood vessels. Color Flow Mapping (CFM) imaging is one such approach. With CFM imaging, a number of pulses are directed to each line-of-sight in a color box, and the returning echoes are used to determine flow direction (towards or away from the transducer) in the color box. A color flow map with colors that indicate flow direction is generated and overlaid over the B-mode image to show flow direction relative to the underlying vessel, etc. structure in the B-mode image.

CFM imaging, relative to B-mode imaging, consumes the majority of each frame, even with a color box that is significantly smaller than the B-mode image. The transducer elements are switched between B-mode and CFM imaging for respective imaging. The pulses transmitted for CFM imaging (e.g., 10-16 each frame) along each color scan line of the image give a frequency shift at each area of measurement, and this frequency shift is displayed as a color pixel. The scanner repeats this for several lines to build up the color image, which is superimposed over the B-mode image. CFM imaging may have to produce many color points of flow information for each frame.

For CFM imaging, the pulse-repetition frequency (PRF) determines a maximum velocity that can be unambiguously measured. That is, where the flow being measured is greater than the half of the PRF, aliasing occurs, and flow moving towards the transducer may be interpreted by the system and displayed as flow moving away from the transducer, and vice versa. Unfortunately, as framerate as well as color sample density is clinically important, it is not always possible to acquire color information at a PRF that allows for unambiguous separation of flow moving towards the transducer from flow going away from the transducer.

Slower flow (e.g., diastole flow, flow close to vessel walls, etc.) may not be identified using a higher PRF. As such, a lower PRF can be employed to measure slower flow even though there will be aliasing in other vessels with faster flow. In this instance, to reduce confusing the user, color maps are created so that the transition from the most positive velocity to the most negative velocity occurs for color that appear approximately equally bright to the user but have different hues. Unfortunately, with strong aliasing, it becomes difficult to look at these images, which result in the user setting a lower limit for the PRF.

There is also a coupling to the fidelity of the acquired color flow images. The raw color flow images are often very noisy and are often of low spatial resolution so that they require significant image processing in order to appear aesthetically pleasing and provide the user diagnostic confidence. As most image processing algorithms such as smoothing and upsampling algorithms are not designed for aliasing, image processing of even mildly aliased images creates significant artifacts in the processed color flow images and these artifacts make users question the diagnostic confidence in the imaging information and therefore avoid lower PRFs even though these images correctly interpreted provide additional useful clinical information.

SUMMARY

Aspects of the application address the above matters, and others.

In one aspect, a method includes receiving ultrasound echo signals produced in response to a pulsed ultrasound field interacting with anatomical tissue and flow of structure therein. The method further includes generating electrical signals indicative thereof. The method further includes beamforming the electrical signals producing beamformed data. The method further includes constructing a real-time image of the anatomical tissue with the beamformed data. The method further includes constructing a de-aliased color images of the flow with the beamformed data. The method further includes visually presenting the real-time image of the anatomical tissue with the de-aliased color images of the flow superimposed thereover.

In another aspect, an ultrasound system includes a transducer array configured to transmit a pulsed field beam into a scan field of view, receive echo signals produced in response to the pulsed field interacting with anatomical tissue and flow of structure therein, and generate electrical signals indicative thereof. The ultrasound imaging system further includes a beamformer configured to process the electrical signals and produce beamformed data. The ultrasound imaging system further includes an image processor configured to process the beamformed data and generate a real-time image of the anatomical tissue. The ultrasound imaging system further includes a color flow mapping processor configured to process the beamformed data and generate a de-aliased color images of the flow. The ultrasound imaging system further includes a rendering engine configured to visually display the real-time image of the anatomical tissue with the de-aliased color images of the flow superimposed thereover.

In another aspect, apparatus includes a beamformer configured to beamform signals indicative of received echo signals produced in response to a pulsed field interacting with anatomical tissue and flowing structure therein. The apparatus further includes an image processor configured to process the beamformed signals and generate an image of the anatomical tissue. The apparatus further includes a color flow mapping processor configured to process the beamformed signals and generate a de-aliased color images of the flowing structure. The apparatus further includes a display configured to visually display the image of the anatomical tissue with the de-aliased color images of the flowing structure overlaid thereover.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
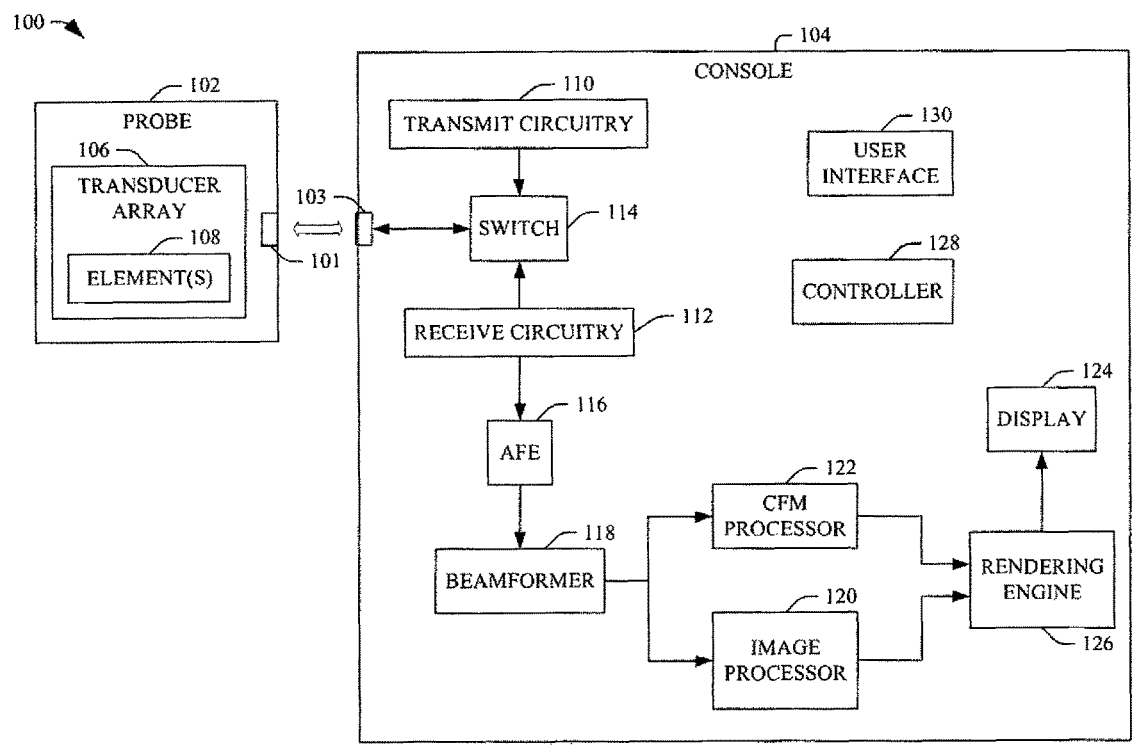
FIG. 1 schematically illustrates an example ultrasound system with a color flow mapping processor.

FIG. 1 illustrates an example ultrasound imaging system 100 configured for at least concurrent B-mode and CFM imaging.

The ultrasound imaging system 100 includes a probe 102 and an ultrasound console 104, which interface through suitable complementary hardware and/or wireless interfaces 101 and 103. The probe 102 includes a transducer array 106 with one or more transducer elements 108. Examples of suitable arrays include 64, 128, 192, 256, and/or other elements arrays, including larger and smaller arrays, and multi-dimensional arrays. The array 106 can be linear, curved, and/or otherwise shaped, fully populated, sparse and/or a combination thereof, etc.

The one or more transducer elements 108 are configured to convert an excitation electrical signal to an ultrasound pressure field and vice versa. The one or more transducer elements 108 are selectively excited via the excitation electrical (pulsed) signal, which cause at least a sub-set of the transducer elements 108 to transmit an ultrasound signal into an examination or scan field of view. Transmit circuitry 110 is configured to generate the excitation signal, or a set of radio frequency (RF) pulses that are conveyed to the transducer array 106. The transmit circuitry 110 is configured to generate excitation signals for B-mode imaging and for CFM imaging.

The one or more transducer elements 108 also receive echo signals (ultrasound pressure fields) and generates analog electrical signals indicative thereof. The echo signals, in one instance, are generated in response to the transmitted ultrasound signals interacting with structure, such as blood cells, flowing in a portion of a vessel and/or other tissue in a region of interest. Receive circuitry 112 is configured to receive the analog electrical signals. The receive circuitry 112 may be configured to pre-condition the received analog electrical signals for further processing.

A switch 114 controls with circuitry, the transmit circuitry 110 or the receive circuitry 112, is in electrical communication with the one or more transducer elements 108 at any given time. For example, the switch 114 electrically connects the transmit circuitry 110 with the one or more transducer elements 108 for transmit operations, and electrically connects the receive circuitry 112 with the one or more transducer elements 108 for receive operations. In a variation, separate switches are used.

An analog front end (AFE) 116 includes at least an amplifier and an analog to digital converter (ADC). The amplifier amplifies the analog electrical signals (e.g., from a micro-volt level to a voltage range of ADC), and the ADC digitizes the amplified signals. A beamformer 118 beamforms the digital signals, e.g., via delay-and-sum beamforming and/or other beamforming. The beamformer 118 outputs the beamformed data (e.g., receive-beams of RF-data).

An image processor 120 processes beamformed data corresponding to the B-mode acquisition. For B-mode imaging, this includes generating a sequence of focused, coherent echo samples along focused scanlines of a scanplane. The image processor 120 can also be configured to generate an A-mode, C-mode, Doppler, and/or other ultrasound imaging mode image.

A CFM processor 122 processes beamformed data corresponding to the CFM acquisition and generates color flow images. As described in greater detail below, in one non-limiting instance the CFM processor 122 processes a time series of color flow images, some of which are aliased, to produce another series of color flow images that is de-aliased. The de-aliasing is based on the assumption that small changes in the flow estimates from frame to frame are less likely than large changes. The de-aliased images can be presented modulo the original range and/or using "speculative" color flow mapping shown as they were estimated after de-aliasing. The combination allows a user to apply a lower pulse-repetition frequency, which would otherwise result in aliasing from faster flow, to produce an image of fast flow without aliasing or, simultaneously, an image of slow flow and fast flow without aliasing. The de-aliasing allows clear visualization of aliased flow making it possible to apply low pulse repetition frequencies to maintain framerate and/or to clearly see slow and fast flow simultaneously.

A display 124 is configured to display images. A rendering engine 126 displays the B-mode image with the CFM superimposed thereover, e.g., via the display 124. A controller 128 is configured to control one or more of the components of the ultrasound imaging system 100. Such control can be based on available modes of operation such as B-mode and/or CFM mode, etc. A user interface 130 includes one or more input devices such as a keyboard, a trackball, a mouse, a touch sensitive screen, etc. configured to allow a user to interact with the system 100.

It is to be understood that one or more of the components of the system 100 (e.g., the processors 120 and/or 122, the controller 128, etc.) is implemented by at least one processor (e.g., a central processing unit (CPU), a microprocessor, or the like) executing computer readable instructions encoded, embedded, stored, saved, etc. on a non-transitory computer readable storage medium (which excludes transitory medium), such as physical memory and/or other non-transitory medium. The at least one processor can also execute instructions carried by a signal, carrier wave, and transitory medium.

The transducer array 106 and the console 104 are shown as separate entities in electrical communication. In a variation, the transducer array 106 and the console 104 are supported in a same housing (e.g. a single unitary scanner) and/or are part of a same device. The illustrated console 104 includes the display 124 and the user interface 130. In a variation, the display 124 and/or the transducer array 106 and the console 104 are separate entities in electrical communication via wireless and/or hardwired. The console 104 can be integrated and part of a mobile cart with movers such as wheels, casters, etc., or rest on a table, desk, etc., and does not include movers and is not integrated into a cart.

Figure 2:
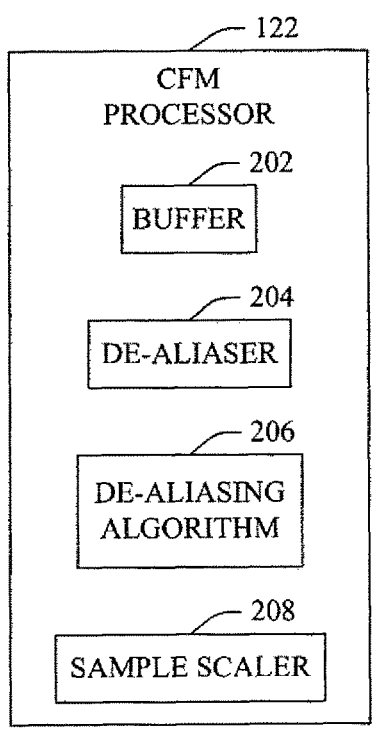
FIG. 2 schematically illustrates an example of the color flow mapping processor.

FIG. 2 schematically illustrates an example of the CFM processor 122. In this example, the CFM processor 122 includes a buffer 202 that stores images, a de-aliaser 204, a de-aliasing algorithm 206, and a sample scaler 208.

The de-aliaser 204 de-aliases an aliased color image based on a reference non-aliased color image store in the buffer 202 using the algorithm 206 and/or other de-aliasing algorithm. In one instance, this includes comparing, on a sample by sample basis, a sample in the image being de-aliased with a corresponding sample of the reference image. Sample by sample processing allows each pixel to be independently de-aliased. In a variation, the comparing is performed pixel group-wise. The current now de-aliased image is used to de-alias the next color image. This is repeated for all desired color images.

With the algorithm 206, if the change in sample value is greater than an expected change, then the sample is considered to be aliased, and the aliased value is replaced with an expected value. If the change in sample value is in line with the expected change, then the sample value is left unaltered. Pseudo-code for an example of the algorithm 206 is described next.

function [a]=de-alias(inp,ref,lmax)
    a=inp=current frame;
    b=ref=reference frame;
    c=a;
    lmax=size of display range+1, if inp are integers, or size of display range, if inp are floating point values;
    d1=abs(b−a);
    d2=abs(a+lmax−b);
    d3=abs(a−lmax−b);
    mymin=min(min(d1,d2),d3);
    c(d2==mymin)=c(d2==mymin)+lmax;
    c(d3==mymin)=c(d3==mymin)−lmax;
    a=c;

The following provides non-limiting examples for a single sample using the above pseudo-code. The examples include examples where aliasing exists (scenarios 1 and 4) and example where there is no aliasing (scenarios 2 and 3). Where aliasing is present, the sample value is replaced, and where aliasing is absent, the sample value is retained.

Scenario 1:
    a=(−)75; b=54; lmax=256; c=a=(−)75
    d1=129; d2=127; d3=385
    mymin=d2
    a=c(d2)=c+lmax=(−)75+256=181
    Scenario 2:
    a=75; b=54; lmax=256; c=a=75
    d1=21; d2=277; d3=235
    mymin=d1
    a=c=75
    Scenario 3:
    a=(−)75; b=(−)54; lmax=256; c=a=(−)75
    d1=21; d2=235; d3=277;
    mymin=d1
    a=c=(−)75
    Scenario 4.
    a=75; b=(−)54; lmax=256; c=a=75
    d1=129; d2=385; d3=127
    mymin=d3
    a=c(d3)=c−lmax=75−256=(−)181

The sample scaler 208 scales the samples. With the above examples, for an integer display range of [−128;+127] (given lmax=127−(−128)+1) the sample scaler 208 scales the de-aliased color images back to the display range. Temporarily unwrapping the data to the larger range allows for other processing of the data, as described below. Where the other processing is omitted, the sample scaler 208 simply scales the de-aliased samples. For example, scaling scenarios 1 and 4 by a constant factor, e.g., of 0.5, would result in values of 90 (or 91) and −90 (or −91), both of which are inside the display range of [−128;+127]. Where the reference frame is already de-aliased, it can have a larger range. Aliasing can be handled at least for changes in velocity from frame to frame is less than 128.

In one instance, the current image is de-aliased via two separate and competing processing chains of the de-aliaser 204. One of the processing chains is as described above and uses the current de-aliased image as the reference image to de-alias the next image. The other processing chain uses the current (non, de-aliased) image as the reference image to de-alias the next image. In one instance, the output of the processing chain which identifies fewer samples as being aliased is used to de-alias the image. This processing chain is well-suited for instance where the velocity changes too much from frame to frame because of a low framerate, estimation noise, and/or color flow holes due to initial color discrimination. In one instance, both the de-aliased image and the non-de-aliased image are smoothed, e.g., via spatial filtering, before being used as a reference image. Such filtering tends to make the reference image less noisy.

The following describes an example approach determining which of the de-aliased image or the non-de-aliased image to de-alias a current image. With this approach, a number of "strange" transitions (i.e. discontinuities) in two candidate images, i.e. the de-aliased image that is based on the previous image, and the de-aliased image that is based on the previous, de-aliased image. For any given pixel position, a spatial windowing function is used to determine which of the two reference images performs better, and that reference image is used for that pixel position. A "strange" transition (discontinuity) is conceptually a big difference by spatially adjacent pixels. Pseudo-code for this approach is described next.

```
function [e, num] = findDiscontinuities(z,e,lmax)
    num = 0;
    for i=2:size(z,1)
        for j=2:size(z,2)
            x = z(i,j);
            a = z(i,j−1);
            b = z(i−1,j);
            c = z(i−1,j−1);
            px = a+b−c;
            pxa = a+b−c+lmax;
            dx = abs(x−px);
            dxa = abs(x−pxa);
            if dxa<dx
                e(i,j) = 1;
                    num = num+1;
            end
        end
    end
```

With the above pseudo-code, for a given sample position (i,j), a good spatial predictor px(i,j) for x(i,j) is a sample value crated by three previous samples, namely the one directly above it, b, the previous sample in the same row, a, and the sample c, which has the same row coordinate as b and the same column coordinate as a. If abs(a+b−c−x) is larger than abs(a+b−c−x+lmax), then it is reasonable to believe that aliasing occurs at that sample position which is therefore "strange."

Figure 3:
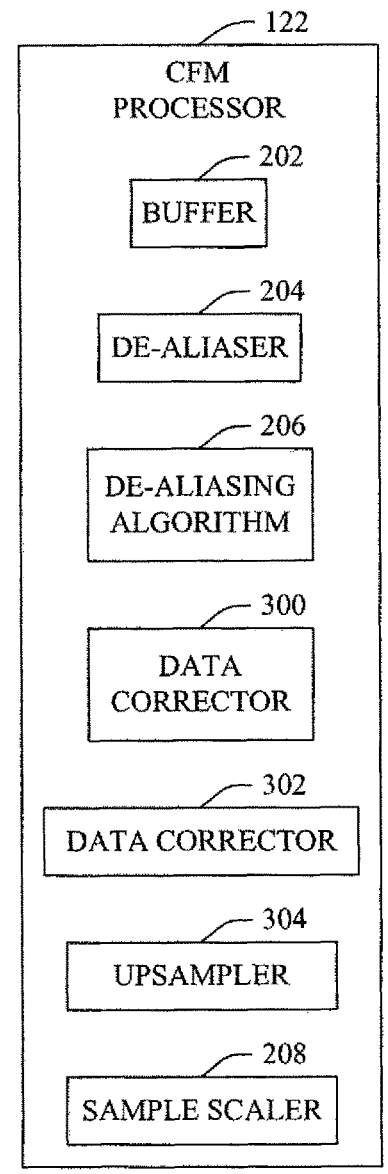
FIG. 3 schematically illustrates another example of the color flow mapping processor.

FIG. 3 schematically illustrates another example of the CFM processor 122. This example is similar to the example described in connection with FIG. 2 but additionally includes, a data corrector 300, a smoother 302 and an upsampler 304. As briefly described above, temporarily unwrapping the data to the larger range allows for other processing of the data. Examples of other processing include correcting, smoothing and/or undersampling samples.

The data corrector 210 generates color sample estimates for missing samples, which cannot be restored by post-processing. The color estimate can provide a plausible appearance. In one instance, the data corrector 210 employs a spatial median filter to generate the color estimates. Other approaches are also contemplated herein. For example, another approach leverages the correlation between the samples from frame to frame. For this, the output is delayed by one frame, for example. The data corrector 210 corrects for missing data where the sample value is zero with a non-zero value. Remaining missing data can be corrected using via median filtering.

The smoother 302 smoothes the color samples. In one instance, this includes applying a lateral median filter. A size of the lateral median filter may be chosen to be a function of the line density since median filtering may compromise spatial resolution, which would be particularly evident from the size of the smallest single color pixel. Such filtering is well-suited for applications where the color samples are acquired in blocks and without transmit interleaving to soften up the block boundaries. The smoother 302 may also apply an n×m finite impulse response filter. For this, each input sample is compared to the average of all nm input samples, and if the absolute difference exceeds that of the input sample plus or minus 256 the average, then the input sample is modified with plus or minus 256 prior to being used. In one instance, the filter is applied only when all nm modified input samples belong to one of the following intervals: ]−256;0[,]0;256[,]−512;−256[,]256;512[.

The upsampler 304 upsamples the color samples. In one instance, this includes upsampling to 4×4 the original resolution. This may soften any blocky appearance due to the absence of transmit interleaving, where the color lines generated from the same transmit shots are highly correlated, and this correlation manifests itself by a staircase appearance at the vessel boundaries. The upsampler 304 can apply an interpolation filter that ensures the staircase appearance becomes much less pronounced. The upsampling may also significantly improve the appearance of noise samples, which are desired to become more round while not occupying a larger area due to the upsampling.

FIGS. 4-9 illustrate an example of the approach described herein. In these images, background gray 400 represents no flow, pixels of a vessel 402 darker than the background gray 400 represent negative flow values, and pixels in of the vessel 402 lighter than the background gray 400 represent positive flow values.

Figure 4:
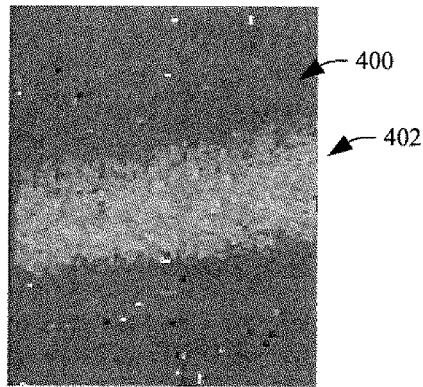
FIG. 4 illustrates a color image of the common carotid artery with slow, unidirectional flow.
Figure 5:
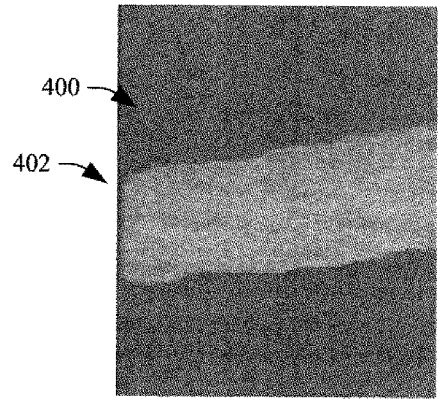
FIG. 5 illustrates the color image of FIG. 4 after visual enhancement.

In FIG. 4, the pixels in the vessel 402 are lighter than the background gray indicating positive flow. FIG. 5 shows a visually enhanced image in FIG. 5 after using one or more of the data corrector 300, smoother 302, and/or upsampler.

Figure 6:
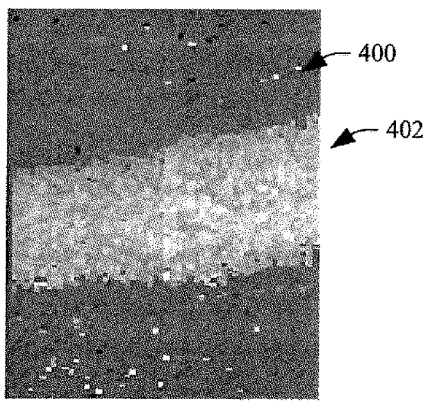
FIG. 6 illustrates a next color image with somewhat faster, positive flow.
Figure 7:
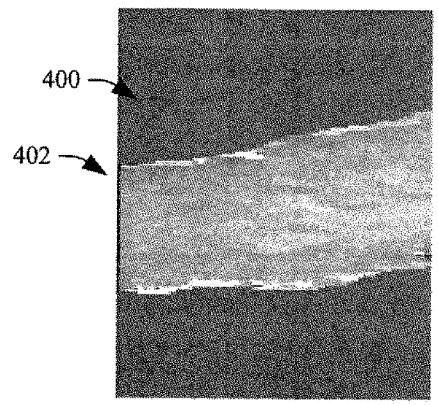
FIG. 7 illustrates the color image of FIG. 6 after visual enhancements.

FIG. 6 represents a current image. Pixels in the vessel 402 include lighter gray pixels indicating positive flow. The de-aliaser 204, based on the FIGS. 4 and/or 5, determines no aliasing is needed and retain the pixel values. FIG. 7 shows a visually enhanced image in FIG. 6 after using one or more of the data corrector 300, smoother 302, and/or upsampler.

Figure 8:
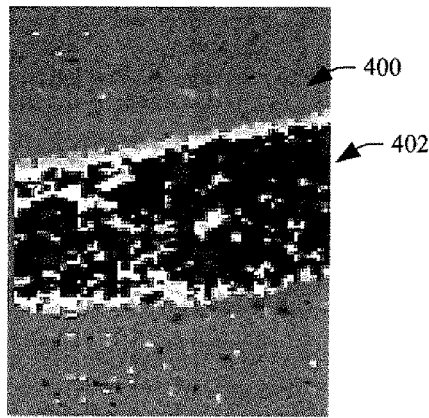
FIG. 8 illustrates a next aliased color image.

FIG. 8 represents a next image. Pixels in the vessel 402 include darker gray and lighter gray pixels indicating negative and positive flow. The de-aliaser 204, based on the FIGS. 6 and/or 7, determines the darker gray pixels represent aliasing and replaces these values as described herein with expected pixel values representing positive flow.

Figure 9:
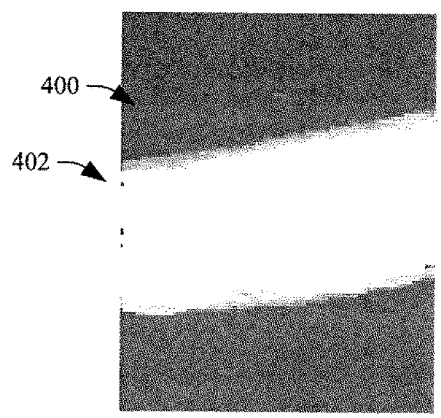
FIG. 9 illustrates the color image of FIG. 8 after de-aliasing and visual enhancement.

FIG. 7 shows a visually enhanced image in FIG. 6 after using one or more of the data corrector 300, smoother 302, and/or upsampler. FIG. 9 shows the de-aliased image after applying the data corrector 300, smoother 302, and/or upsampler 304. FIG. 9 shows the expected pattern of lower values near the vessel walls and higher values in the middle of the vessel.

Figure 10:
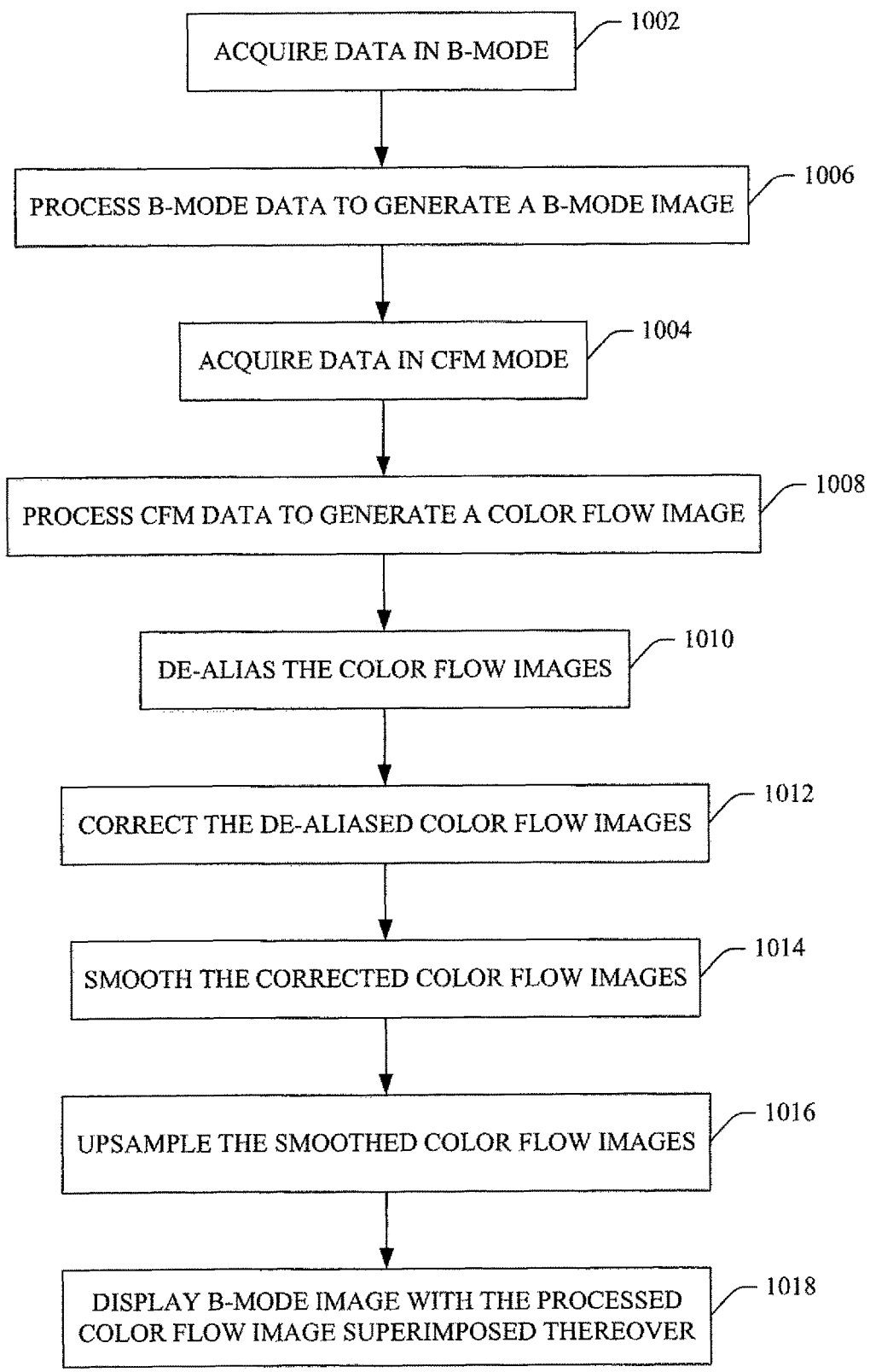
FIG. 10 illustrates an example method in accordance with an embodiment herein.

FIG. 10 illustrates an example method in accordance with an embodiment herein.

It is to be understood that the following acts are provided for explanatory purposes and are not limiting. As such, one or more of the acts may be omitted, one or more acts may be added, one or more acts may occur in a different order (including simultaneously with another act), etc.

At 1002, a transducer array is employed to acquire B-mode data, as described herein and/or otherwise.

At 1004, the B-mode data is processed to generate a B-mode image, as described herein and/or otherwise.

At 1006, the transducer array is employed to acquire CFM data, as described herein and/or otherwise.

At 1008, the CFM image is processed to generate a color flow image, as described herein and/or otherwise.

In a variation, at least one of acts 1006 and 1008 can occur before at least one of acts 1002 and 1004.

At 1010, the CFM image is de-aliased, as described herein and/or otherwise, e.g., using a previous de-aliased image or an image with no aliasing.

At 1012, the de-aliased CFM image is corrected for missing data, as described herein and/or otherwise.

At 1014, the corrected CFM image is smoothed, as described herein and/or otherwise.

At 1016, the smoothed CFM image is upsampled, as described herein and/or otherwise.

In a variation, one or more of acts 1012, 1014 or 1016 are omitted.

At 1018, the resulting CFM image is visually displayed superimposed over the B-mode image. An uncorrected CFM image can additionally or alternatively be visually displayed.

It is to be appreciated that the approach described herein represents at least an improvement in a technology or technical field and/or an improvement in ultrasound system itself. Current technology/ultrasound systems are limited in at least that the PRF is constrained such that faster flow is susceptible to aliasing when real-time imaging faster flow, and faster flow is susceptible to aliasing when imaging slower flow with a low PRF. The approach described herein overcomes these technology limitations, providing de-aliased color images with the same PRF, which would otherwise result in aliased color images.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
receiving ultrasound echo signals produced in response to a pulsed ultrasound field interacting with anatomical tissue and flow of structure therein;
generating electrical signals indicative thereof;
beamforming the electrical signals producing beamformed data;
constructing a real-time image of the anatomical tissue with the beamformed data;
constructing a de-aliased color image of the flow with the beamformed data by:
creating a time series of color images; and de-aliasing, on a pixel by pixel basis, a current color image of the time series of color images based on a previous color image of the time series of color images by:
  determining a first absolute value of a difference between a pixel value at a pixel location of the current color image with a pixel value at the same pixel location of the previous color image;
  determining a second absolute value of a summation of a negative value of the difference and a predetermined value;
  determining a third absolute value of a subtraction of the negative value of the difference and the predetermined value;
  identifying which of the first, the second and the third absolute values is a smallest of the values; and
  de-aliasing the pixel of the current color image based on which of the first, the second and the third absolute values is identified as the smallest of the values; and
visually presenting the real-time image of the anatomical tissue with the de-aliased color image of the flow superimposed thereover.

2. The method of claim 1, wherein the previous color image is a de-aliased color image.

3. The method of claim 1, wherein the previous color image is a non, de-aliased color image.

4. The method of claim 1, further comprising:
de-aliasing the pixel of the current color image by replacing the value of the pixel with an expected value of the pixel in response to identifying the second or the third absolute values as the smallest of the values.

5. The method of claim 4, further comprising:
retaining the value of the pixel in response to identifying the first absolute value as the smallest of the values.

6. The method of claim 1, further comprising:
de-aliasing the current color image of the time series of color images based on a previous color image of the time series of color images that was de-aliased producing a first de-aliased color image, wherein the de-aliasing the current color image of the time series of color images based on the previous color image of the time series of color images produces a second de-aliased color image;
identifying which of the first and the second de-aliased color images de-aliased fewer pixels of the current color image;
utilizing the identified one of the first and the second de-aliased color images as the de-aliased color image.

7. The method of claim 6, wherein the first and the second de-aliased color images are concurrently generated via parallel processing chains.

8. An ultrasound system, comprising:
a transducer array configured to transmit a pulsed field beam into a scan field of view, receive echo signals produced in response to the pulsed field interacting with anatomical tissue and flow of structure therein, and generate electrical signals indicative thereof;
a beamformer configured to process the electrical signals and produce beamformed data;
an image processor configured to process the beamformed data and generate a real-time image of the anatomical tissue;
a color flow mapping processor configured to process the beamformed data and generate a de-aliased color images of the flow by:
  generating a time series of color images; and
  de-aliasing a current color image of the time series of color images based on a previous color image of the time series of color images by:
    computing a first absolute value of a difference between a pixel value at a pixel location of the current color image with a pixel value at the same pixel location of the previous color image;
    computing a second absolute value of a summation of a negative value of the difference and a predetermined value;
    computing a third absolute value of a subtraction of the negative value of the difference and the predetermined value; and
    de-aliasing the pixel of the current color image based on which of the first, the second and the third absolute values is a minimum value; and
a rendering engine configured to visually display the real-time image of the anatomical tissue with the de-aliased color images of the flow superimposed thereover.

9. The system of claim 8, wherein the previous color image is a de-aliased color image.

10. The system of claim 8, wherein the previous color image is a non, de-aliased color image.

11. The system of claim 8, wherein the color flow mapping processor retains the value of the pixel in response to identifying the first absolute value as the minimum value.

12. The system of claim 11, wherein the color flow mapping processor de-aliases the pixel of the current color image by replacing the value of the pixel with an expected value of the pixel in response to identifying the second or the third absolute values as the minimum.

13. The system of claim 12, wherein the value of the pixel of the current color image has a first sign, the expected value has a second sign, one of the first and second signs is positive, and the other of the first and second signs is negative.

14. The system of claim 8, wherein the color flow mapping processor:
de-aliases the current color image of the time series of color images based on a previous color image of the time series of color images that was de-aliased producing a first de-aliased color image, wherein the de-aliasing the current color image of the time series of color images based on the previous color image of the time series of color images produces a second de-aliased color image; and
utilizes the first or the second de-aliased color images that de-aliases a fewest number of pixels as the de-aliased color image.

* * * * *